United States Patent [19]

Charlton et al.

[11] Patent Number: 4,540,520

[45] Date of Patent: Sep. 10, 1985

[54] COMPOUND USEFUL IN DETECTING ION AND METHOD OF PREPARING IT

[75] Inventors: Steven C. Charlton, Elkhart, Ind.; Roger L. Fleming, Niles, Mich.; Authur L. Y. Lau, Elkhart, Ind.

[73] Assignee: Miles Laboratories, Inc., Elkhart, Ind.

[21] Appl. No.: 493,981

[22] Filed: May 12, 1983

[51] Int. Cl.³ .............................................. C07C 97/18
[52] U.S. Cl. ................................................ 260/396 N
[58] Field of Search ................................... 260/396 N

[56] References Cited

FOREIGN PATENT DOCUMENTS 639191  4/1962  Canada ........................... 260/396 N

OTHER PUBLICATIONS

H. D. Gibbs, Chem. Review, (13), 1927, pp. 291–319.
D. Svobodova et al., Mikrochimica Acta, 1978, pp. 251–264.

Primary Examiner—Glennon H. Hollrah
Assistant Examiner—Raymond Covington
Attorney, Agent, or Firm—Edward H. Gorman, Jr.

[57] ABSTRACT

A novel compound is disclosed having the structure

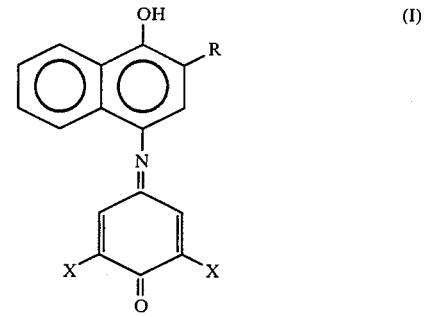

in which R is lower alkyl and X is halogen or pseudohalogen. Also disclosed in a novel process for preparing the compound which comprises the steps of combining a compound having the structure

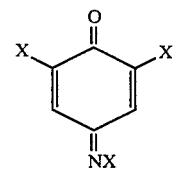

in which X is a halogen or pseudohalogen, and a compound having the structure

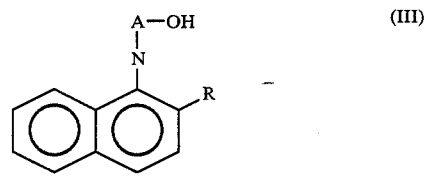

in which R is lower alkyl and A is lower alkylidene to produce a first reaction mixture; adjusting the pH of the first reaction mixture to at least about 8 to produce a second reaction mixture; and recovering the compound or its salt from the second reaction mixture.

6 Claims, No Drawings

COMPOUND USEFUL IN DETECTING ION AND METHOD OF PREPARING IT

INTRODUCTION

The present invention relates to a novel compound useful in the measurement of ions, in particular ions in aqueous solution, and to a method for its preparation. The invention makes possible a quick, facile way of assaying ions whereby results are available to the assayist momentarily after merely contacting a test sample solution with a test means or device containing the compound. There is no need for cumbersome, expensive electronic equipment such as ion-specified electrodes, flame photometers, atomic absorption spectrophotometers or the like. Nor is it necessary to resort to time-consuming wet chemistry techniques such as titration and other laboratory procedures. The compound of the present invention enables the analyst to merely contact the test sample with a strip device or similar test means configuration, and observe any color change.

The determination of aqueous ion concentration has application in numerous technologies. In the water purification art, calcium concentration must be carefully monitored to assess the degree of saturation of an ion exchange resin deionizer. Measurement of sodium and other ions in seawater is important in the preparation of drinking water aboard a ship at sea. Measurement of the potassium level in blood aids the physician in diagnosis of conditions leading to muscle irritability and excitatory changes in myocardial function. Such conditions include oliguria, auria, urinary obstruction and renal failure due to shock.

Needless to say, a quick, facile method for determining ion concentration would greatly enhance the state of these technologies, as well as any others where such rapid, accurate determinations would be beneficial. Thus, for example, if a medical laboratory technician could accurately measure the potassium or calcium level of a serum or whole blood sample in a matter of seconds or minutes, not only would such rapid results aid the physician in diagnosis, but also laboratory efficiency would increase manyfold. The present compound is the linchpin of such a test, being a reporter substance which, when present in the composition containing an ionophore for the ion to be detected, produces a detectable response to the presence of the ion.

BACKGROUND OF THE INVENTION

Prior to the present invention, phenolic imine compounds were prepared by the so-called Gibbs Reaction. H. D. Gibbs, *Chem. Review* 13, 291–319 (1927). See also D. Svobodova, et al., *Mikrochimica Acta*, pp. 251–264 (1978). These references, the contents of which are incorporated herein by reference, describe the coupling of phenols with imines in accordance with

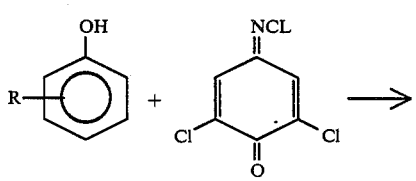

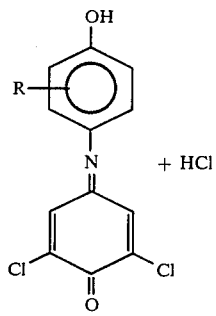

Such reactions are useful in a test for determining the presence phenols.

The novel compound of the present invention is not only useful as a reporter substance for detecting ions in a test sample, but provide stability during storage and is relatively free from interfering side reactions in a sample.

DEFINITIONS

Certain terms used in the present discussion should at this point be mentioned to assure that the reader is of the same mind as the author as to their respective meanings. Thus the following definitions are provided to clarify the scope of the present invention, and to enable its formulation and use.

3.1 The term "ionophore" includes molecules capable of forming a complex with a particular ion, in some instances to the substantial exclusion of others. For example the cyclic polypeptide, valinomycin, binds selectively to potassium ions in solution to form a cationic complex. Also included in the term are coronands, cryptands and podands.

3.2 The term "nonporous" is intended to mean substantially impervious to the flow of water. Thus a nonporous carrier matrix is one which substantially precludes the passage of water through it, one side to the other. For example, a polyvinyl chloride film would be considered for the purposes herein as being nonporous.

3.3 A "reporter substance" is a compound which is capable of interacting with an ionophore/ion complex to produce a color change or other detectable response. Thus, a reporter substance can be one which is relatively colorless in the non-ionized state, but which colors when in the presence of a complex of an ionophore and an ion. The compound of the present invention is such a substance, i.e., it produces color or change in light reflectance in the presence of such a complex.

3.4 By "interacting" is meant any coaction between a reporter substance and an ionophore/ion complex which leads to a detectable response. An example of the reporter substance interacting with the complex is in the case where the reporter is changed by the complex from a colorless to a colored state, such as in the case of 2-methyl-4-(3',5'-dichlorophen-4'-one)-indonaphth-1-ol.

3.5 The term "detectable response" is meant herein as a change in or occurrence of a parameter in a test means system which is capable of being perceived, either by direct observation or instrumentally, and which is a function of the presence of a specific ion in an aqueous test sample.

3.6 The term "lower alkyl", as used in the present disclosure includes an alkyl moiety, substituted or unsubstituted, containing about 1–4 carbon atoms. Included in the meaning of lower alkyl are methyl, ethyl, n-propyl, isopropyl, n-butyl, sec-butyl and tert-butyl. These may be unsubstituted, or they may be substituted provided any such substituents not interfere with the operation or functioning of the presently claimed test means or device in its capability to detect ions. "Lower alkylidene" is used in the same context as "lower alkyl", but designates an alkylene group (i.e., a divalent alkyl) having 1-4 carbon atoms. Thus, lower alkylidene includes methylene, ethylidene, n-propylidene, isopropylidene, n-butylidene, sec-butylidene and tert-butylidene.

3.7 By "pseudohalogen" is meant atoms or groups of atoms which, when attached to an unsaturated or aromatic ring system, affect the electrophilicity or nucleophilicity of the ring system, and/or have an ability to distribute an electrical charge through delocalization or resonance, in a fashion similar to the halogens. Thus, whereas halogen signifies Group VII atoms such as F, Cl, and I, pseudohalogens embrace such moieties as —CN, —SCN, —OCN, —N₃, —COR, —COOR, —CONHR, —CF₃, —CCl₃, —NO₂, —SO₂CF₃, —SO₂CH₃, and —SO₂C₆H₄CH₃, in which R is alkyl or aryl.

SUMMARY OF THE INVENTION

The present invention resides in the discovery of a novel compound which has been found useful as a reporter substance, or indicator, in a test for the presence of a specific ion or group of ions in an aqueous test sample. The compound is one having the structure

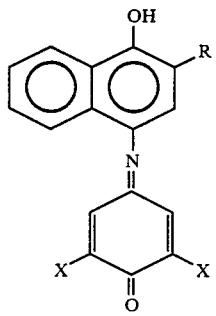
(I)

in which R is lower alkyl and X is a halogen such as F, Cl, Br or I, or X is a pseudohalogen. in preferred embodiments, R is methyl and/or X is Cl.

In addition to the novel compound, the present invention also comprises a process for preparing it. Basically, the process involves the reaction between a 2,6-dihaloquinone-4-haloimide and N-[2'-(lower alkyl)-1'-naphthyl]-aminoalkanol. The former compound has the structure

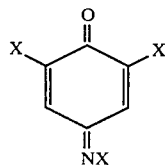
(II)

in which X is as defined above. The N-naphthylaminoalkanol has the structure

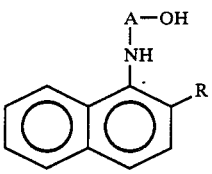
(III)

in which R is lower alkyl and A is lower alkylidene. Upon combining these precursor compounds to form a first reaction mixture, the pH is adjusted to at least about 8 to produce a second reaction mixture. Compound I is then isolated from the second reaction mixture. In a preferred embodiment, the isolation step includes acidifying the second reaction mixture to a pH in the range of about 2-4. Preferred reactants are 2,6-dichloroquinone-4-chloroimide and N-[1'-(2'-methyl)-naphthyl]aminoethanol. These latter compounds produce the specific version of compound (I) having the name 2-methyl-4-(3',5'-dichlorophen-4'-one)indonaphth-1-ol.

PREPARATION OF THE COMPOUND OF THE PRESENT INVENTION

Because of the relative instability of compound (II) it is preferable to use a nonaqueous solution in combining it with (III). Acetone has been found particularly suited for this step, but of course other solvents such as other ketones and alcohols might be equally compatible. Such a determination is easily within the ability of the routineer, given the present disclosure.

Generally it is preferred to combine stoichiometrically equal amounts of (II) and (III) as solutions to form a first reaction mixture. The pH of the first mixture is then adjusted to at least about 8 using a suitable base, thereby forming a second reaction mixture. Preferably an aqueous buffer (pH in the range of about 8 to 11) is utilized. It has been found that good results are obtained with a 100 mM aqueous solution of 3-(cyclohexylamino)propanesulfonic acid which has been adjusted to pH 10 with LiOH.

Following the formation of the second reaction mixture, the product (I) is recovered by any suitable means. Acidification of the second reaction mixture is one such means of recovery, in that the basic form of (I), i.e., the deprotonated form which is soluble in water, is rendered insoluble through addition of of acidic hydrogen ions. Thus addition of 1N HCl with rapid stirring causes precipitation of (I), and the precipitate is easily recovered via centrifugation. Ideally the second reaction mixture is acidified to a pH in the range of about 2-4.

Further purification can be effected by dissolving the precipitate in a suitable solvent, such as acetone, and passing this solution through a purification procedure, such as recrystallization, column chromotography or thin layer chromatography.

USE OF COMPOUND (I)

The compounds of the present invention find use as reporter substances, or indicators, in a system for measuring specific ions or groups of ions. Such a system comprises, in addition to (I), an ionophore and a carrier matrix. The carrier matrix has incorporated within it the ionophore, compound (I) either being incorporated with the matrix or added separately to the test sample being analyzed. If the ion to be assayed is present in the test sample, it can complex with the ionophore, and the formation of such complex causes (I) to change color. Typically a blue color is formed.

In a preferred use, the ionophore and (I) are incorporated with the carrier matrix in such a way as to be substantially isolated from the aqueous test sample. For example, the ionophore and (I) can be taken up in a solution of vinyl chloride/vinylidene chloride copolymer in a suitable solvent and cast as a film on a polyester substrate film. Despite the hydrophobicity of such a film, the ion under analysis can penetrate it by complexing with the ionophore. Such penetration is to the exclusion of other test sample components. The formation of the ionophore/ion complex evokes the appearance of color in the film due to interacting of the complex with compound (I).

Although the mechanism of the color formation is not known, it may well be due to the formation of an ion having a resonant structure capable of absorbing light at certain wavelengths. It is probable that Compound (I) exhibits tautomerism, in accordance with

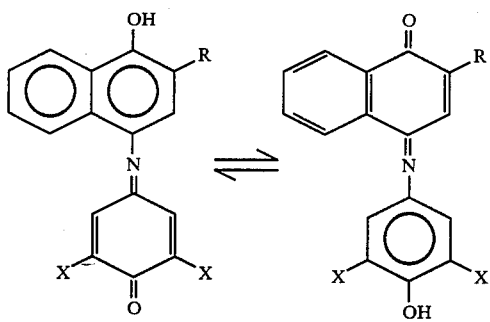

In the presence of a charged ion/ionophore complex, through a mechanism not thoroughly understood, it is theorized that the tautomer could lose a hydroxyl proton to become a resonating ion in accordance with

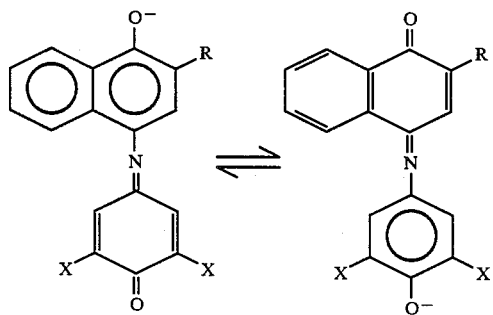

such a resonant structure theory is a plausible explanation for the generation of blue color observed when a film containing valinomycin and (I) is contacted with aqueous potassium.

EXAMPLES

A series of experiments was conducted whereby a unique synthesis procedure was utilized in preparing the novel compound (I). Following its preparation, (I) was then tested as to its utility as a reporter substance in a test means and device for measuring ions in solution. The preparative procedures utilized, as well as the evaluation are described in the following examples.

Preparation of
2-Methyl-4-(3′,5′-dichlorophen-4′-one)indonaphth-1-ol

The captioned compound (hereafter, MEDPIN) was prepared in accordance with the following procedure.

Equimolar amounts of 2,6-dichloroquinone-4-chloroimide (DQCI) and N-[1′-(2-methyl)naphthyl-]aminoethanol (MeNAE) were mixed in acetone to a concentration of 100 mM of each solute. A brown solution resulted.

To a one mL (milliliter) portion of this solution, was added 6 mL of 100 mM CAPS buffer (pH=10), CAPS buffer is an aqueous solution of 3-(cyclohexylamino)-propanesulfonic acid titrated to pH 10 with LiOH. The resulting solution was red in color.

1N HCl was added dropwise to the red solution with efficient mixing until the pH dropped to about 2.6. The solution became turbid rapidly, a brick-red precipitate forming. Care was taken not to allow the pH below about 1.9 to avoid product decomposition.

The mixture was then centrifuged, the precipitate dried at RT under nitrogen, and redissolved in 3 mL acetone. After standing in a refrigerator at 4° C. for 30 minutes, the liquid was passed onto a silica gel column and eluted with a 1:4 mixture of ethyl acetate and toluene. A reddish brown band formed in the column.

Thin layer chromatography of the product on a silica gel plate eluted by a 1:4 solution of ethyl acetate and toluene gave a single spot at Rf 0.76.

The fractions containing the product were pooled, and the solvent removed under vacuum in a rotary evaporator. The purified product can be stored as a dried powder or in acetone at 0° C.

Characterization of the Product of 7.1

A series of experiments was undertaken to characterize the compound isolated in example 7.1, and to elicit its structure.

Mass spectrum analysis yielded a strong 3-line pattern at 331, 333 and 335. Such a pattern is indicative of the presence of two chlorine atoms.

Elemental analysis gave evidence of an empirical formula of $C_{17}H_{11}NO_2Cl_2$ in accordance with the following data:

|  | % C | % H | % N | % O | % Cl |
| --- | --- | --- | --- | --- | --- |
| Found | 61.79 | 3.76 | 3.98 | 9.50 | 20.69 |
| Calculated | 61.45 | 3.31 | 4.22 | 9.64 | 21.39 |

A molecular weight of 332 was deduced from mass spectroscopy.

Proton nuclear magnetic resonance (nmr) spectra showed the presence of seven groups of protons in addition to those of the solvent. The most upfield signal of the spectrum is due to methyl protons split by the neighboring lone proton. The next signal is due to two equivalent single protons on a benzene ring. The third signal, a quarter, is attributable to a proton at the 3-position of a naphthalene ring, split by three methyl protons. The remaining signals further downfield are due to four protons on the 5-, 6-, 7- and 8-positions of a naphthalene ring. Interactions among these signals give rise to this complex ABCD-type spectrum.

The results of these experiments are, in their sum total, strong evidence that the product of example 7.1 has the structure of compound (I) in which R is methyl and X is Cl.

Use of Compound (I) in Detecting Potassium

A solution was prepared containing 6.7 mg/mL valinomycin and 1.67 mg/mL MEDPIN in o-nitrophenyloctyl ether. A buffered gelatin solution was prepared using 3.13 g Type I gelatin (Sigma Chemical Co.) which had been dialyzed at 10° C. to remove ionic impurities, and 20.8 g of dionized water. To this was added 0.25 mL of a buffer prepared by adjusting 1M Trizma base (Sigma Chemical Co.) to pH 8 with HCL (Baker) and then to pH 5 with acetic acid (Baker).

The oil and gelatin solutions were mixed and placed in a 12-37 mL mini sample container for a Waring Blender (Fisher Scientific) and blended for 2 minutes at high speed.

After allowing 15-30 minutes at 45° C. for bubbles to rise, the emulsion was spread onto a polyester film support which had been pretreated to accept gelatin (40 GAB 2S, 3M Co.). The film was spread to a thickness of $6.75 \times 10^{-3}$ inches, (#75 Mayer Rod, RDS Co., Webster N.Y.) The film was air dried, then $0.2 \times 0.4$ inch pieces were mounted onto polystyrene film support handles using double-faced adhesive tape (Double Stick, 3M Co.) to form test devices.

Test samples were prepared containing 0, 0.2, 0.6, 0.6, 0.8 and 1.1 mM KCl, 100 mM tris-Cl pH 8.5. These concentrations correspond to those found in serum diluted ninefold. A 30 μL (microliter) sample drop was placed on the reagent portion of a test device and incubated at 37° C. in a Seralyzer ® (Ames Division, Miles Laboratories, Inc.) reflectance spectrophotometer for 2.5 minutes, at which time the reflectance at 640 nm (nanometers) were measured. The reflectance data is tabulated below.

| $K^+$ (mM) | $(K/S)^2$ |
|---|---|
| 0 | 0.2048 |
| 0.2 | 1.4945 |
| 0.6 | 5.3038 |
| 1.1 | 8.4158 |

The data shows a linear correlation between $K^+$ concentration and $(K/S)^2$.

$(K/S)^2$ is defined as $$(K/S)^2 = \frac{(1-R)^4}{4R^2}$$

in which R is the fraction of reflectance from the test device, K is a constant, and S is the light scattering coefficient of the particular reflecting medium. The above equation is a simplified form of the well-known Kubelka-Munk equation (See Gustav Kortüm, "Reflectance Spectroscopy", pp 106-111, Springer Verlag, New York (1969).

The above data shows that potassium concentration corresponds linearly to $(K/S)^2$. Moreover, the data shows that various concentrations can be accurately measured.

What is claimed is:

1. A compound having the structure

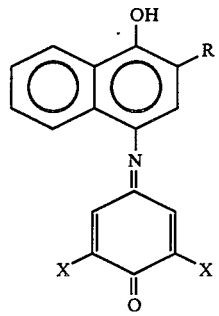

in which R is lower alkyl and X is halogen or pseudohalogen.

2. The compound of claim 1 in which R is methyl.

3. The compound of claim 2 in which X is Cl.

4. A process for preparing the compound of claim 1, the process comprising the steps of combining, in a nonaqueous solvent, a compound having the structure

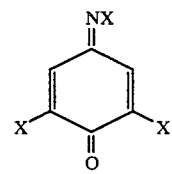

in which X is a halogen or pseudohalogen, and a compound having the structure

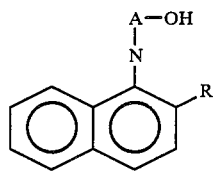

in which R is lower alkyl and A is lower alkylidene, to produce a first reaction mixture;

maintaining the pH of the first reaction mixture to at least about 8 to produce a second reaction mixture; and recovering the compound of claim 1 or its salt from the second reaction mixture.

5. The process of claim 4 in which the steps of recovering comprises lowering the pH to the range of about 2-4.

6. The process of claim 4 in which the step of combining comprises combining 2,5-dichloroquinone-4-chloroimide and N-[1'-(2'-methyl)naphthyl]aminoethanol and the compound of claim 1 is 2-methyl-4-(3',5'-dichlorophen-4'-one)indonaphth-1-ol.

* * * * *